United States Patent [19]

Draenert

[11] Patent Number: 5,015,101

[45] Date of Patent: May 14, 1991

[54] APPARATUS AND PROCESS FOR MIXING AND FILLING

[76] Inventor: Klaus Draenert, Gabriel-Max-Str. 3, D-8000 Munich 90, Fed. Rep. of Germany

[21] Appl. No.: 542,634

[22] Filed: Jun. 25, 1990

Related U.S. Application Data

[63] Continuation of Ser. No. 414,595, Sep. 27, 1989, abandoned, which is a continuation of Ser. No. 133,064, Nov. 17, 1987, abandoned.

[30] Foreign Application Priority Data

Mar. 21, 1986 [DE] Fed. Rep. of Germany ....... 3609672

[51] Int. Cl.⁵ .............................................. B01F 5/12
[52] U.S. Cl. ..................................... 366/349; 222/137; 366/130; 366/184; 366/333
[58] Field of Search ............... 366/129, 255, 190, 256, 366/332–335, 197, 348, 349, 130, 203; 222/137, 145

[56] References Cited

U.S. PATENT DOCUMENTS

| | | | |
|---|---|---|---|
| 2,584,202 | 2/1952 | Harp, Sr. ............................ | 366/197 |
| 2,973,187 | 2/1961 | Wehmer ............................. | 366/139 |
| 3,164,303 | 1/1965 | Trautmann ......................... | 366/333 |
| 3,190,619 | 6/1965 | Penney et al. ..................... | 604/82 |
| 3,358,971 | 12/1967 | Steinback, Jr. .................... | 366/139 |
| 3,560,162 | 2/1971 | Mittleman ......................... | 366/256 |
| 3,700,215 | 10/1972 | Hardman ........................... | 366/332 |
| 3,718,139 | 2/1973 | Hanford ............................. | 604/87 |
| 3,735,900 | 5/1973 | Geres ................................. | 366/129 |
| 3,779,371 | 12/1973 | Rovinski . | |
| 4,177,184 | 7/1981 | Solomon ............................ | 366/139 |
| 4,185,072 | 1/1980 | Pudenbaugh et al. ............. | 366/139 |
| 4,371,094 | 2/1983 | Hutter, III ......................... | 366/333 |

FOREIGN PATENT DOCUMENTS

| | | | |
|---|---|---|---|
| 909723 | 9/1972 | Canada ............................... | 206/222 |
| 0170120 | 2/1986 | European Pat. Off. . | |
| 0800455 | 8/1958 | United Kingdom ................ | 604/87 |

*Primary Examiner*—Robert W. Jenkins
*Attorney, Agent, or Firm*—Kinney & Lange

[57] ABSTRACT

The invention relates to an apparatus and a process for mixing a compound comprising at least two components and especially to an apparatus and a process for mixing bone cement and filling it into an applicator (130). The apparatus comprises a mixing bowl (100) and a sealing means (140) which can be connected to the applicator (130). The applicator (130) can be moved within the mixing bowl (100) relative thereto. Due to the relative motion of the applicator (130) and the mixing bowl (100), the bone cement is mixed and filled into the applicator (130).

19 Claims, 8 Drawing Sheets

APPARATUS AND PROCESS FOR MIXING AND FILLING

This is a continuation of application Ser. No. 07/414,595 filed on Sept. 27, 1989, which is a continuation of application Ser. No. 07/133,064 filed on Nov. 17, 1987, both abandoned.

The invention relates to an apparatus and a process for mixing a compound comprising at least two components. In particular, the invention relates to an apparatus and a process for mixing bone cement and filling it into an applicator.

The term "mixing" is generally understood to mean the insertion of the particles of one substance into the particles of other substances. The aim is to obtain as homogenous as possible a distribution of the various components of the compound, for instance to initiate or promote a chemical reaction between the components such as the following polymerization of a two-component or multi-component compound.

Various kinds of mixing processes and mixing apparatus are known. The process of mixing can be carried out by stirring, mingling, rolling, kneading, emulsifying, suspending, dissolving or by means of ultrasonic radiation.

The known mixing processes and mixing apparatus, however, have the disadvantage that impurities, such as air, can enter into the mixing system and that the gas occlusions already contained at the beginning of the mixing process in the substances to be mixed and those which form during the actual process of mixing, for instance via a chemical reaction, cannot be removed from the mixing system. A further disadvantage which often occurs is that the mixing vessel is not identical to the vessel in which the compound is to be further processed. It then becomes necessary to transport the compound, a fact that causes problems, especially in reactions which occur in the compound itself such as polymerization.

Special problems arise in the processing and mixing of bone cement and when filling the same into the vessel from which the bone cement is later applied.

The bone cement is usually made of cold polymerizing two-component resins which anchor the components of artificial joints into the bony bed. The bone cement hardens as soon as it has been applied. Due to its plastic properties, it anchors the components of the prosthesis into the bony bed by interlocking. Polymethylmethacrylates (PMMA) have been used as bone cement for several years now. They comprise a powdery bead polymer superficially dissolved in a liquid monomer. Said liquid monomer then polymerizes, thus embedding the powdery bead polymer. In the mixing phase, the monomer surrounds the approximately pellet-shaped polymer powder. This firstly leads to a bloating of the pellets in which a considerable amount of air bubbles are trapped. The process of polymerization occurs exothermically. In addition to the trapped air bubbles, when the polymer pellets are surrounded by the monomer, so-called "lee phenomena" appear regularly; they are the sign of insufficient cross-linking of the polymer pellets. Also, the monomeric liquid evaporates during the process of exothermal polymerization which leads to the fact that in the end the hardened bone cement is riddled with bubbles of various ethiology and genesis.

As a rule, the polymer powder is added to the monomer and then mixed in a bowl using a spatula. In the processing phase which follows the mixing phase, the bone cement is applied to the bony bed, e.g. to the femoral medullary canal or to the bony acetabulum, both of which have been prepared for the anchoring of the cemented prosthesis components; the application is usually performed by hand and sometimes using a syringe. A syringe of this kind is described in DE-A-28 01 706 and in EP-A1-170 120, for instance. By using a bone cement syringe, markedly better results were achieved in view of the cement anchorage in the bone than with the conventional method in which the bone cement is filled in with the fingers.

To date there are hardly any papers which deal with the mixing phase and bloating phase of the bone cement and with the artefact-free insertion thereof into the syringe system.

The further processing of the bone cement stirred in the mixing bowl in the above-mentioned fashion depends on its viscosity. Bone cement of a very low viscosity can be poured from the bowl into the cartridge of the bone cement syringe; the problem, however, is that the stream of bone cement flowing into the syringe can be very easily diverted, for instance via electrostatic charging, so that the sides of the cartridge and the opening thereof are almost always covered with bone cement. Highly viscous bone cement cannot be poured at all. It has to be removed and kneaded by hand into order to press out the largest of the air occlusions. The bone cement is then rolled into a sausage-shaped mass which can be inserted into cartridge. When manually processing the cement, not only does one have to wait until the bone cement no longer sticks to the surgical gloves, but the cement mixture also remains unprocessed in the most important stage of the bloating phase and the pre-polymerization phase that follows.

The attempts made to date to try and solve the problem of mixing the cement in a so-called "closed system" have not managed to produce a mixture better than that produced by hand.

Hence the object of the invention is to provide a process and an apparatus with which a compound comprising at least two components can be mixed rapidly and without bubbles and can then be placed into the vessel in which the further processing of the compound is to take place.

A further object of the invention is to provide an apparatus and a process for mixing bone cement and filling it into an applicator with which apparatus and process bone cement comprising several components can be mixed rapidly, without bubbles and without being touched by the surgeon and can then be filled into an applicator from which the bone cement is to be applied to the bony bed.

These objects are achieved by the features of the patent claims.

The invention is based on the principle of pushing the substances to be mixed, preferably a curable two-component system such as a mixture of polymer powder and monomers, out of the opening or taper of a first vessel into a second vessel. In order to improve the process of mixing, the compound is then preferably pushed back into the first vessel through the opening of the second vessel. This process can be repeated several times and is called "extrusion mixing".

The first vessel or mixing vessel is preferably cup-shaped or cylinder-shaped with one closed and one open end. The second vessel, which is the applicator at the same time and in which the compound is further processed once it has been blended, is preferably cylinder-shaped, too, and has one open end. The other end of the second vessel can be closed by means of a cap or a plunger. The outer circumference of the second vessel, preferably the open end thereof, is provided with a sealing means, preferably comprising several flexible discs or lamellae.

In order to mix and transfer the compound, the second cylindrical vessel or hollow member is axially pushed with its open end onwards into the first vessel which contains the substances to be mixed or which have already been partially mixed. By means of this relative motion of the two vessels, the compound is forced through the opening of the second vessel as the sealing means seals off the space between the inner wall of the first vessel and the outer wall of the second vessel in such a manner that only gas can escape between them, but not the substances to be mixed.

When applying the above principle to mixing bone cement and filling it into an applicator, the monomer is firstly placed into a mixing bowl whereupon the polymer powder is added to the formulation and stirred in with a spatula made of metal, plastic or wood. Instead of removing all of the cement paste with the spatula, or pouring it out if the cement has a low viscosity, as in conventional processes, the idea of the invention is to insert the cartridge-shaped applicator with its mounted sealing means through the opening of the mixing cup. If the sealing means is fashioned as a cylindrical member with a central, tubular opening and several disc-shaped lamellae, said means can be mounted to any kind of commercially available cartridge by means of adapters, preferably small rings, and can be used in combination with these cartridges. The cylindrical vessel described in EP-A1-170 120 is the one preferably used as the applicator or cartridge. By pushing in the cartridge and the sealing means connected thereto, the cement which has been pre-mixed with the spatula is forced into the cartridge through the central opening of the sealing means. The diameter of the opening can be either the same or smaller than that of the cartridge. The extruding effect leads to a more thorough mixing of the bone cement, and it proceeds from the mixing bowl into the cartridge without having been touched by the surgeon's hands. Furthermore, the flowing process presses out large air bubbles.

Instead of a conventional spatula, a round rod advantageously coated with teflon is used to premix the cement. The round rod has the advantage that it does not rupture the compound, but promotes the blending thereof by means of a laminar flow of the layers of the compound. Furthermore, when mixing and removing the bone cement, almost nothing sticks to the teflon-coated round rod.

In order to avoid air occlusions, it is of particular advantage to carry out the mixing of the components, for example the components of the bone cement, under vacuum. For this, the mixing vessel preferably has a surface ground upper rim onto which a lid is mounted. The mixing vessel can be sealed off from the lid using a conical nipple covered with vacuum grease or using a silicon coating. The lid can also be connected to the mixing vessel in a vacuum-tight manner by means of an easily removable flanged joint. The lid has a connection for a tube feed to which a vacuum pump is attached.

The lid preferably has a firm rim which is placed onto the rim of the mixing vessel, and a feed-through for the round rod used in the mixing process. The sealed feed-through for the round rod is preferably arranged within one inner portion of the lid, said inner portion being made of flexible material and the lid being connected in a vacuum-tight fashion, preferably integrally, to the firm rim. The inner portion of the lid can be tent-shaped and can have at its open end the feedthrough which is shaped as an annular feed and is preferably made of rubber or silicon, through which the round rod is fed and which holds said round rod in a vacuum-tight manner. As the inner portion of the lid is flexible, the round rod can be moved in a radial direction within the mixing vessel and can be guided along the inner wall of the mixing vessel so that none of the components to be mixed, for instance no bone cement powder, remains on the inner wall untouched. This is of extraordinary significance for obtaining thorough mixing.

By mixing the bone cement under vacuum, the number of bubbles in the cement can be diminished even further and the mixture can be stirred without almost no bubble formation whatsoever.

Experiments have shown that tall mixing vessels enable a much quicker and more homogenous mixing of the cement paste than wide, shallow mixing bowls which exhibit dead corners. The bottom of the mixing vessel is preferably spherical or concave. When the cartridge is pressed in, the foremost flexible lamella of the sealing means moulds itself to the bottom of the mixing bowl in such a manner that nothing remains in the mixing bowl. It is of particular advantage if the bottom of the mixing bowl is flexible, too, so that complete adaption of the form is assured.

The formation of dead spaces at the upper edge of the cement paste during the flowing process can be avoided if the foremost lamella of the sealing means is also slightly bent or concave so that the cement paste is forced in radially from the outer edge of the mixing cup.

When the cartridge is being pushed in as explained above, both air and the gases released during the process of polymerization can escape between the lamallae of the sealing means. Also, the body of the sealing means can comprise at least one additional valve through which the gases can escape.

Furthermore, it is also possible to produce a vacuum and to evacuate air from the mixing bowl by applying pressure thereto and closing the central opening or the end of the cartridge whilst mechanically compressing the cement at the same time. The result is that the majority of the small air bubbles, too, can be removed from the cement as early as in the mixing process.

When filling the cement into the cartridge it is important that the end facing away from the mixing bowl is not closed or if the cartridge has a cap, that said cap is only loosely mounted to allow the air which is pushed out in front of the cement to escape from the cartridge.

In the system described above, which is called the "half closed system", the second vessel can be a cartridge as used in the bone cement syringe according to EP-A1-170 120 or in similar syringes. In this system, the cement does not have to be touched by the surgeon's or scrub-nurse's hands or surgical gloves prior to its application, which is of great advantage. On the one hand it is a known fact that the monomer can easily penetrate the rubber gloves of the operating team, and more and more allergies to the plastic they are made of have recently become known; on the other hand, the contact-free procedure leads to a considerable reduction in the number of flaws in the cement, and it proceeds more quickly and at an earlier stage into the bone cement pistol for precompression because one does not have to wait for it to set.

The cement can be mixed even more thoroughly by a movable plunger in the second vessel. The plunger or piston seals the interior of the second vessel in a cement-tight, but gas-permeable manner and can be axially pressed into and pulled out of the second vessel via a manipulation apparatus.

By applying this system it is possible to move the compound, for instance the bone cement, in and out of the central opening of the first and second vessel several times. Due to the flow and the extruding effect the components are very thoroughly mixed. Once the compound has been mixed by pushing the second vessel into the first and has been transferred into the first vessel, the plunger is pushed in a downward direction via the manipulation apparatus whilst the first vessel is held fast at the same time. By doing this, the plunger forces the mixture out of the second vessel back into the first vessel, with the second vessel moving in an upward direction in opposition to the plunger and relative to the first vessel. This is due to the fact that the compound applies pressure to the foremost lamella of the sealing means and pushes the sealing means connected to the second vessel in an upward direction. The second vessel is then pushed back into the first vessel, whereupon the compound flows back into the second vessel and the plunger is pushed back. This process can be repeated several times until an intimate blend has been achieved.

In this embodiment it is also possible to leave out the previous mixing and stirring of the components of the compound. This will be explained below, for instance when mixing and filling in bone cement.

First of all the polymer powder is introduced into the second vessel or applicator, the lower opening of which is initially sealed off by a membrane. The other end of the applicator is sealed off by the plunger, and the applicator is pushed down to the bottom of the first vessel which serves as a mixing vessel.

The monomer is in a third vessel which comprises a tip or a needle. Initially the tip can be closed and opened only shortly before being applied. The tip of the monomer vessel is pushed through a reclosable plug on the bottom of the mixing bowl, and by pulling back the applicator, the monomer is sucked into the mixing bowl by the occurring partial vacuum. The monomer vessel is then removed again so that the plug on the bottom of the mixing bowl can reclose. The monomer now dissolves the membrane which is made of a suitable material and has kept the applicator closed to this moment, and the polymer powder is released and can be pushed into the monomer in the mixing bowl by the plunger. The monomer and the polymer powder can then be intimately mixed by repeatedly agitating the plunger and the applicator as explained above. Trapped air can escape through a valve in the sealing means.

The above explained embodiment can be called a "closed system" as the components of the compound, e.g. the bone cement, can be stored separately and never have to be touched by the surgeon's hands whilst being processed, mixed and filled into the applicator, and are not subjected to processing steps such as being stirred with a spatula from which air occlusions could result.

The first vessel (mixing bowl) and the second vessel (applicator) are preferably made of the same material. They can be made of plastic, preferably thermoplastic material such as a polyolefin. The use of poly(4-methyl-1-pentene) or TPX ® is especially preferred. It is also possible to use polycarbonate. The third vessel (monomer vessel) is made of a material which is not affected by the monomer, preferably teflon.

The vacuum lid for the mixing vessel is preferably made of teflon, too, or of the material used for the mixing vessel and the applicator, for instance poly(4-methyl-1-pentene).

In the following the invention will be explained in greater depth using examples relating to mixing bone cement and filling it into an applicator, and using illustrations. The figures show.

Figure 1:
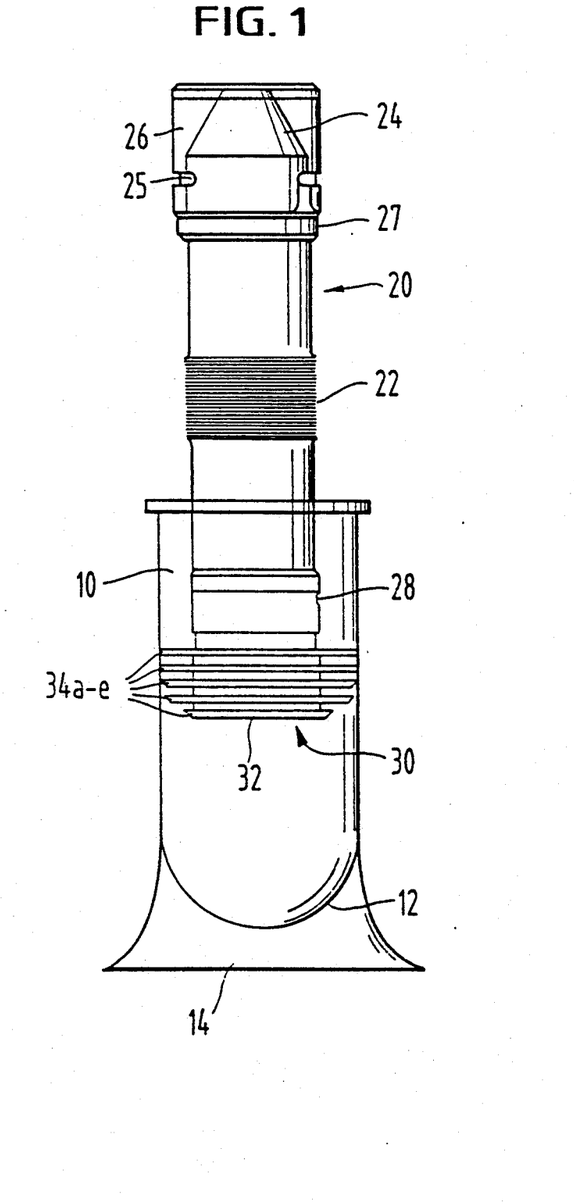
FIG. 1: a first embodiment of the apparatus of the invention for mixing bone cement and filling it into an applicator.

According to FIG. 1, the apparatus of the invention comprises a tall circular cylindrical mixing bowl 10 having a round bottom 12 and an flat base 14.

The applicator 20 is fashioned in the shape of a syringe cartridge and has a corrugated gripping surface 22 and a conical front part 24 serving as a mouth piece for the application. A bayonet closure 25 having a rising thread fastens a closure cap 26 to this end, said cap lying close to a rib 27 which serves as a stopper on the applicator. On the other (during application rear) end of the vessel 20, the sealing means 30 is fastened by an adapter 28. The interior of the tubular body 32 of the sealing means 30 has a central opening and five flexible lamallae 34 a to e on its circumference. The sealing means is made of teflon and the diameter of the lamallae gradually increases starting from the foremost lamella 34 e which faces the bottom of the mixing bowl 10 and has the smallest diameter.

When mixing the bone cement, first the monomer and then the polymer powder is placed into the mixing bowl 10 and mixed with a spatula, preferably a round spatula made of teflon. Then the applicator 20 with its mounted sealing means 30, as shown in FIG. 1, is pushed into the top of the mixing bowl 10 the top of which is open. When doing this the lamellae adapt themselves to the round bottom 12 of the mixing bowl 10 and all of the bone cement is forced through the central opening of the sealing means 30 into the vessel 20. The lamellae 34 are designed in such a way that it is possible for the air above the bone cement and/or the gases which escape during polymerization to escape between the lamellae 34, but the bone cement can only pass through a certain number of the lamellae. The graduated diameter of the lamellae 34 assures that the bone cement cannot pass through all the lamellae even if one allows for a certain process tolerance range.

Once all the bone cement has been filled into the vessel 20 in this way, the adapter 28 with the sealing means 30 is removed from the vessel 20 and the vessel 20 is mounted onto a bone cement syringe such as the bone cement pistol according to EP-A1-170 120. Thus the applicator 20 serves directly as a cartridge for the application of the bone cement.

Figure 2:
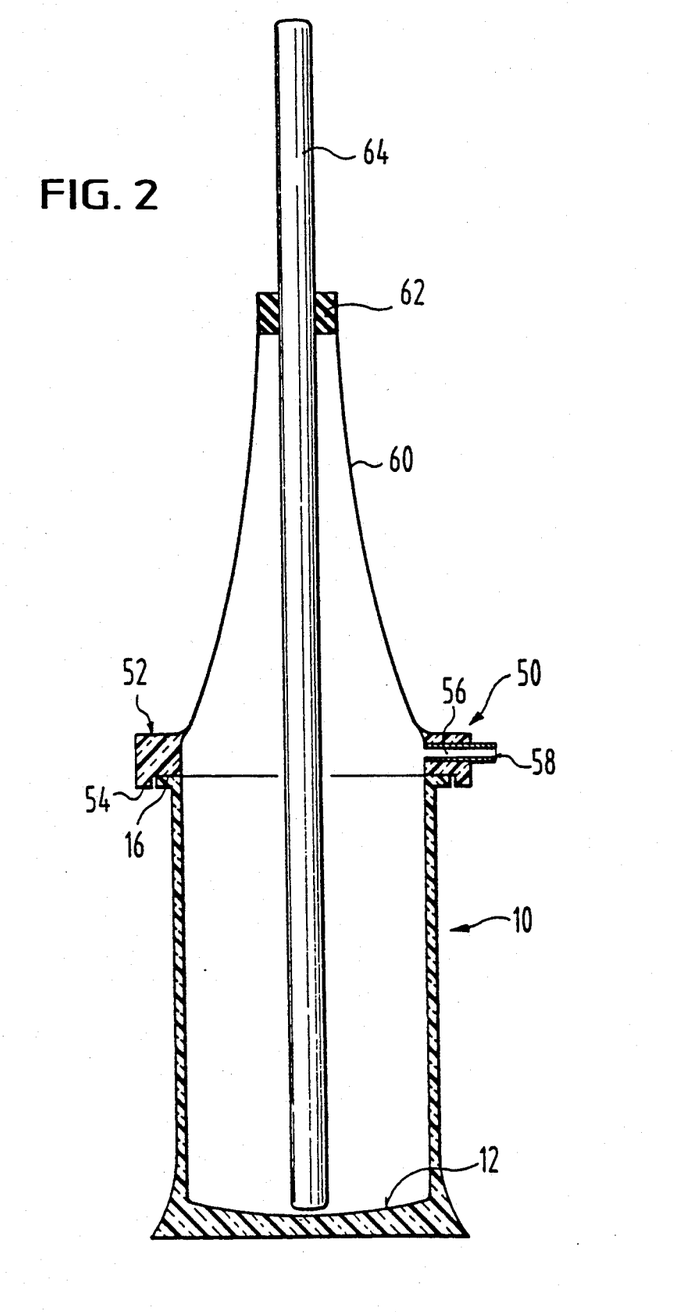
FIG. 2: a similar embodiment to that of FIG. 1 comprising an additional vacuum lid for the mixing vessel.

The mixing bowl 10 according to FIG. 2 is basically the same as the mixing bowl according to FIG. 1 and has a concave bottom 12 and a surface ground upper rim 16. In addition to the mixing bowl according to FIG. 1, the mixing bowl 10 according to FIG. 2 comprises a vacuum lid 50, the firm rim 52 of which lies on the surface ground rim 16 of the mixing bowl 10. A silicon layer can be used to separate the two surfaces of the rim 16 and 52 which contact, but it is also possible to provide a conical nipple in one of the grooves of the rim 16. The outer portion of the rim 52 of the lid 50 has a nose 54 which laps over the rim 16 and prevents the lid 50 from being displaced against the rim 16 of the mixing bowl 10.

Furthermore, the rim 52 of the lid 50 is provided with a feed-through 56 and a connection 58 for connecting a vacuum lead (not illustrated), which leads to pump which is not illustrated either.

In addition to the firm rim 52, the lid 50 has a flexible, tent-shaped inner portion 60. In the illustrated embodiment, the inner portion 60 is integrally connected to the rim 52 and is made of the same material as the rim 52, but is a continuation thereof and thus thinner so that the material of the inner portion 60 exhibits a certain flexibility. Teflon and poly(4-methyl-1-pentene) are especially suitable materials therefor. However, the flexible inner portion 60 can also be connected to the lid 52 by means of a vacuum-tight connection such as a flanged joint and can be made of a different material than the lid 52, such as a plastic film.

An annular feed-through 62 made of an expandable material, preferably sterile rubber or silicon, is welded in a vacuum-tight manner to the upper end of the roof-shaped or tent-shaped inner portion 60. The inner portion 60 with its feed-through 62 can be biased so that it will possess a certain stability. A round rod 64 runs through the flexible feedthrough 62, said rod preferably being made of teflon and being about 8 mm thick.

The apparatus according to FIG. 2 is used under vacuum in about the first 30 seconds of the mixing phase to stir or premix the raw compound of monomer and polymer powder in the mixing bowl 10. As the inner portion 60 of the lid 50 is flexible, the round rod 64 can be moved in a radial direction within the mixing bowl 10 and can also be guided along the inner wall of the mixing bowl 10. It is important that the interior of the lid 50 does not extend past the inner wall of the mixing bowl 10. The round rod is used to prevent the cement from sticking to the rod during stirring and when removing the rod, to prevent the compound from rupturing and to produce a laminar flow of the individual layers of the compound, by means of which the process of blending is promoted.

Once the stirring and mixing phase has been completed, the round rod 64 is removed and the lid 50 of the mixing bowl 10 detached. The bone cement, as explained in FIG. 1, can then be extruded into the applicator.

Figure 3:
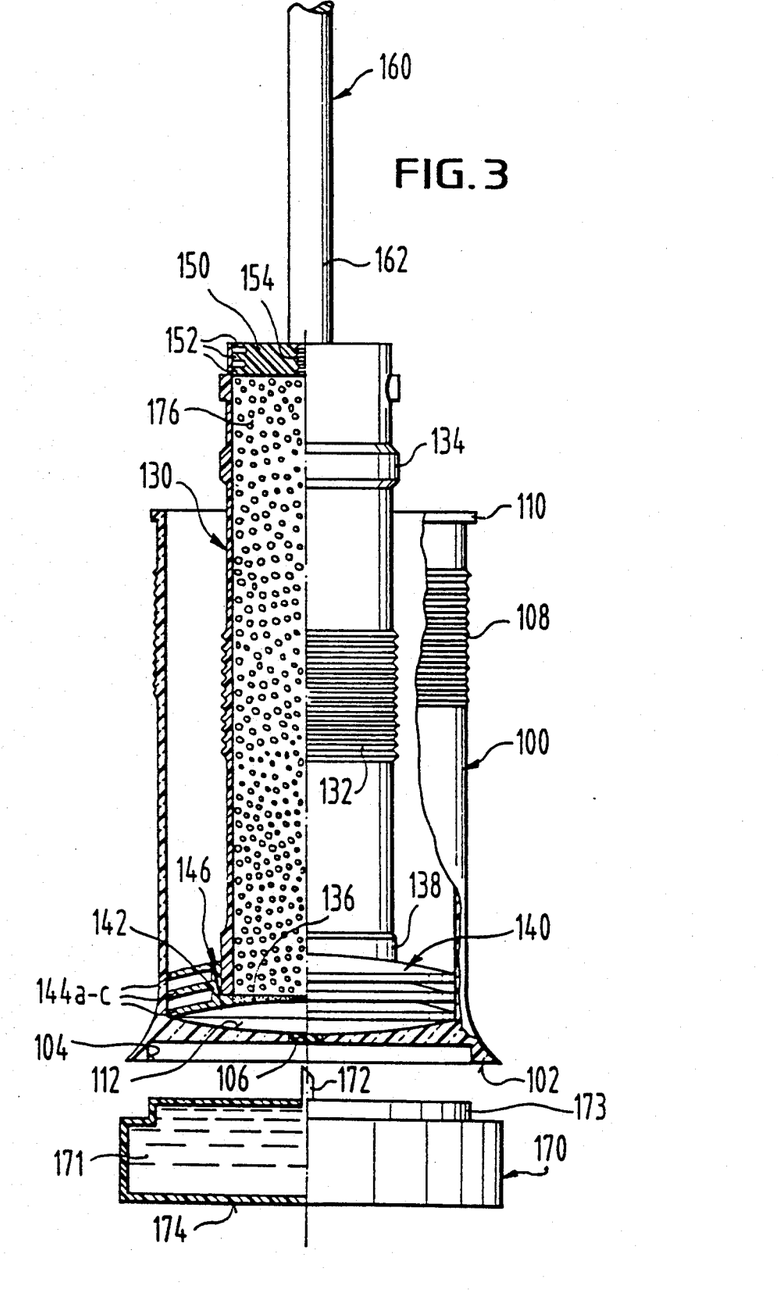
FIGS. 3 to 6: a partial section of a further embodiment of the apparatus of the invention, the plunger being shown in its various positions whilst the process of the invention is being carried out.

FIG. 3 shows an embodiment of the invention which can be used as a "closed system".

The bottom of the circular cylindrical mixing bowl 100 comprises a base 102 with a circular recess 104. A rubber plug 106 is provided in the middle of the bottom. The mixing bowl 100 has a corrugated gripping surface 108 on each side of its circumference and a rim 110 at the top which serves as a reinforcement. The bottom 112 of the mixing bowl 100 is concave.

The applicator 130 also has a corrugated gripping surface 132 and a rib 134. The lower end of the applicator 130 is shut off by means of a membrane 136 which is integral with the applicator 130 or with a sealing means 140, said sealing means being connected to the applicator by means of an adapter 138.

The sealing means 140 is made of teflon and comprises a cylindrical member 142 and three disc-shaped, flexible lamellae 144 a to c. The lamellae 144 seal the inner wall of the mixing bowl 100 in a gas-permeable but liquid-tight and especially cement-tight manner. The foremost lamella 144 c forms a concave surface which opens towards the bottom of the mixing bowl 100. The other lamellae can also be concave. The member 142 is provided with a needle valve, the top of which is gas permeable.

The upper end of the applicator 130 comprises a piston or plunger 150 with several lamellae 152. The plunger 150 seals off the inner wall of the applicator 130 in a cement-tight but gas-permeable manner. The plunger 150 comprises a central inner thread 154 into which a plunger-manipulation apparatus 160 comprising a rod 162 can be screwed.

FIG. 3 also illustrates a monomer vessel 170 for receiving the monomer 171. The monomer vessel 170 comprises a needle or tip 172, a round projection 173 and a flat bottom 174 which serves as a base.

FIG. 3 represents the initial position for the process of the invention. The polymer powder 176 is in the applicator 130 which is distally shut off by the thin membrane 136. The membrane is made of a material which can be dissolved by the monomer being used, preferably a bone cement of the same composition as that of the bone cement to be mixed, such as PMMA, but without an X-ray contrast medium and without a filler. The distal end of the applicator 130 is sealed off from the mixing bowl 100 by the sealing means 140, and the proximal end thereof by the plunger 150.

Once the manipulation apparatus 160 has been screwed into the plunger 150, firstly the monomer vessel 170 and its projection 173 are pushed into the recess 104 in the bottom of the mixing bowl 100 and are held there in a press-fit. At the same time the now open tip 172 of the monomer vessel 170 pierces the plug 106 and the monomer in the monomer vessel 170 reaches the interior of the mixing bowl 100.

Figure 4:
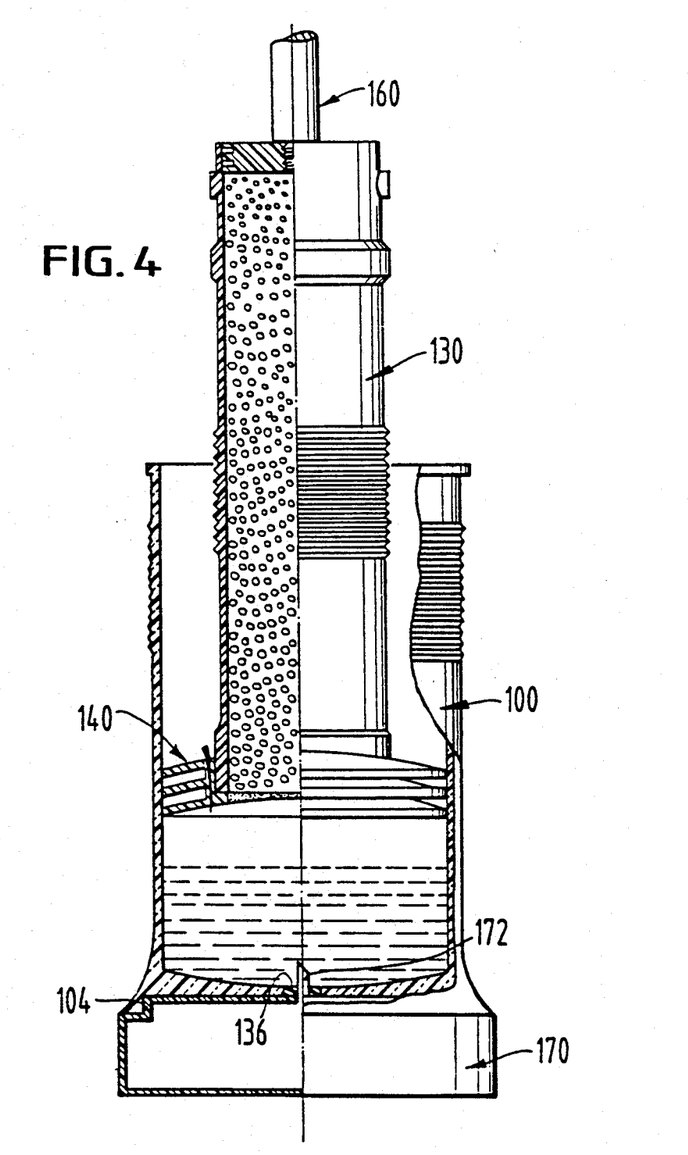

The mixing bowl 100 is held in one hand by its fluting-shaped gripping surface 108, and the applicator 130 which has been connected to the sealing means 140 is held in the other hand, is pulled back and at the same time drawn up like a hypodermic syringe until the occurring partial vacuum causes all the monomer to be sucked up through the needle or tip 172 into the mixing bowl 100. This position is shown in FIG. 4.

By coming into contact with the monomer and its vapour the thin membrane 136 dissolves completely. This does not present a problem as the membrane is made of the same chemical material as the finished bone cement. When the membrane 136 disintegrates, the polymer powder in the applicator 130 is set free and reaches the monomer. In view of a uniform distribution of the polymer pellets and in view of occurring air occlusions, the introduction of the polymer powder into the monomer has advantages over the addition of the monomer to the polymer powder.

Figure 5:
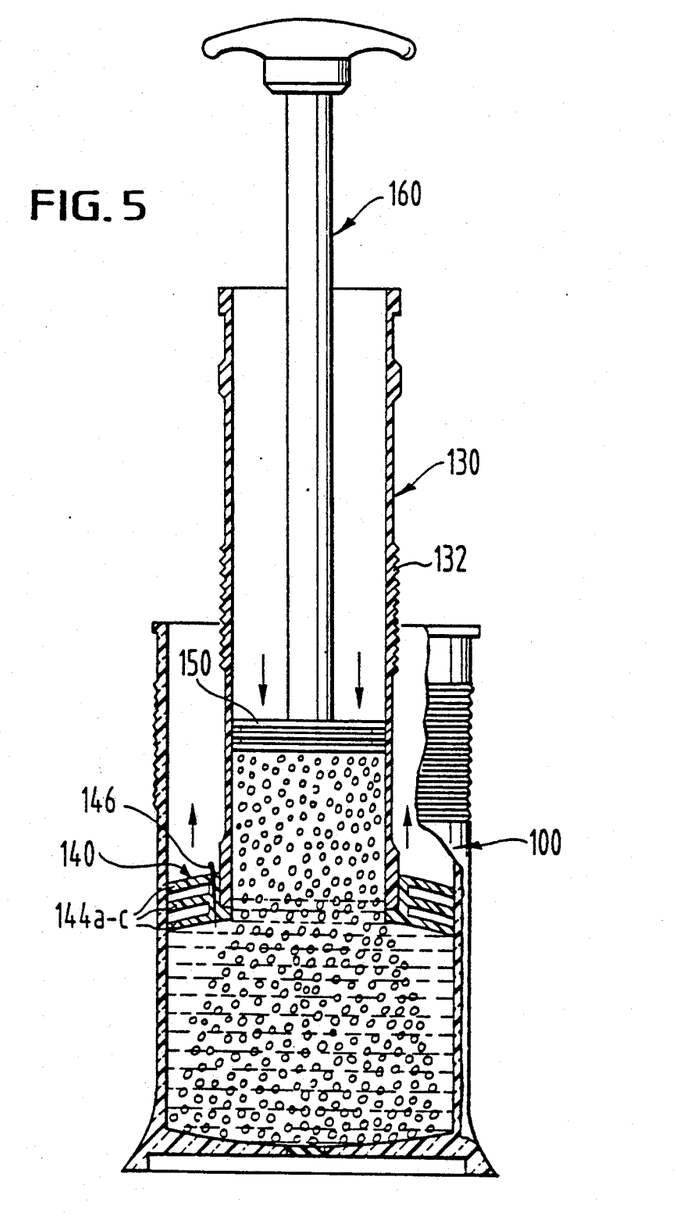

In the next step the plunger 150 is pushed in a distal direction, i.e. downwards, and the rest of the PMMA-membrane 136 is pushed by the plunger 150 into the monomer bath together with the polymer powder and is dissolved there. Whilst the plunger 150 moves in a distal direction, the increased volume of the monomer and the polymer powder pushes the sealing means 140 and the applicator 130 in the mixing bowl 100 in a proximal direction, i.e. upwards, until the polymer powder has been completely pushed out of the applicator 130. The occluded air or the gas bubbles produced during polymerization can escape between the lamellae 144 and the inner wall of the mixing bowl 100 and/or through the one-way needle or ball valve 146. This step is illustrated in FIG. 5, the monomer vessel 170 already having been removed.

Figure 6:
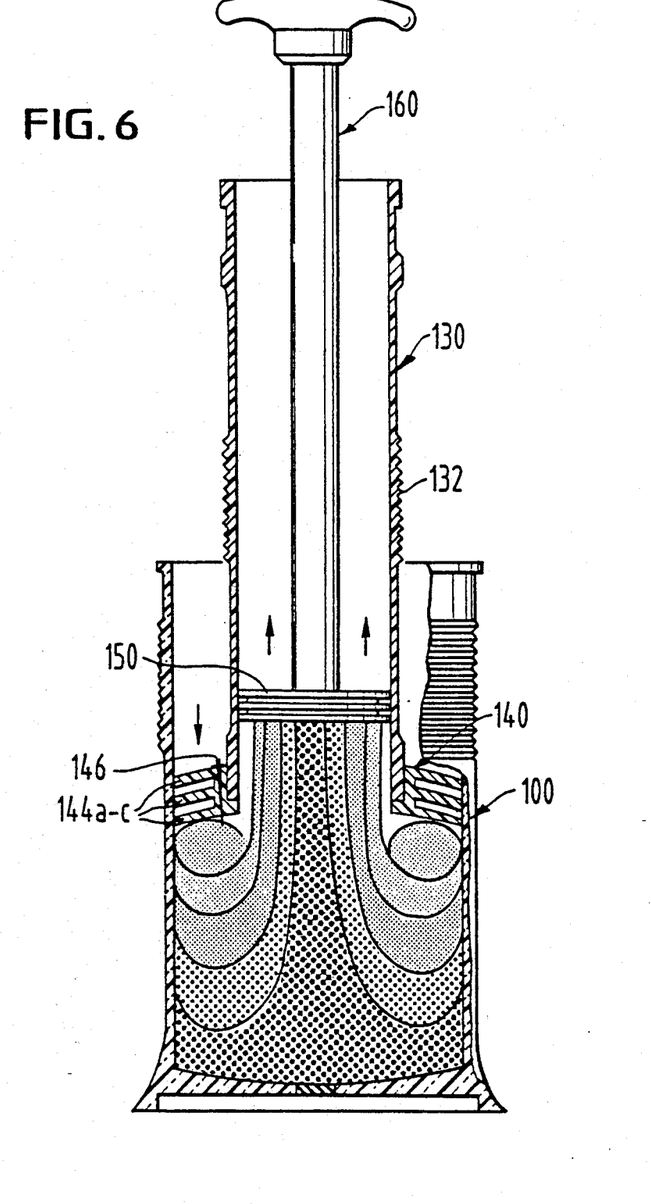

The applicator 130 is then taken by its fluting-shaped gripping surface 132 and pushed down again whilst the mixing bowl 100 is either held or stood up. As the raw compound of the polymer powder and the monomer cannot pass through the sealing means 140, the compression extrudes the raw compound out of the mixing bowl 100 back into the applicator 130 and the bone cement-raw compound pushes the plunger 150 in an upward direction. This usually leads to lamination of such a kind that the cement pastes which contain the most polymer powder form the radially outer layer, whilst the radially inner layers contain more and more monomer. The core of the cone resulting from the process of extrusion is formed by the monomer from the bottom of the mixing bowl. In this way the layer of pure polymer powder is penetrated by the liquid monomer. FIG. 6 represents such an intermediate position. With the concave shape of the lamella 144 c, dead spaces along the sides of the mixing bowl 100 are avoided and the raw compound is radially pushed in an inward direction towards the opening of the applicator without any of it sticking to the wall.

FIG. 6 is a schematic illustration of the laminar flow of the compound during extrusion through the opening into the applicator.

Once the applicator 130 has been pushed down to the bottom of the mixing bowl 100 and the flexible lamella 144 c has moulded itself completely to the concave shape of the bottom 112, all of the bone cement mixture is in the cartridge. By pushing the plunger 150 in a downward direction and holding the mixing bowl 100 at the same time, the compound is then pushed back and lifts up the applicator 130 (see FIG. 5), whereby a mainly laminar flow again occurs. Then the applicator 130 is again pushed down by hand (see FIG. 6). If these process steps are repeated and if the applicator 130 and the plunger 150 are alternately moved in a downward direction, the layers are intimately blended. The process of extrusion can continue to be repeated until the mixing of the bone cement has been completed. Finally, the bone cement mixture is extruded into the applicator 130 for the last time and the plunger 150 is removed from the top by means of the manipulation apparatus 160. Then the adapter 138 is loosened so that the sealing means 140 can be removed, and by means of an adapter (not shown), a mouth piece is mounted to the (in the figure upper) front part of the applicator 130, said mouth piece varying according to whether it is being used for sockets, femurs or knee joints. Once the applicator has been mounted onto a bone cement syringe, e.g. according to EP-A1-170 120, the bone cement can be applied.

Due to the volume increase which occurs when the sealing means is pulled back, a partial vacuum is formed above the mixture which will usually suffice to remove occluded air bubbles from the compound. Said bubbles are no longer pressed into the bone cement during extrusion, but escape through the valve 146 in the sealing means 140.

One may, however, wish to apply an exterior vacuum in order to remove all the gas from the compound.

Figure 7:
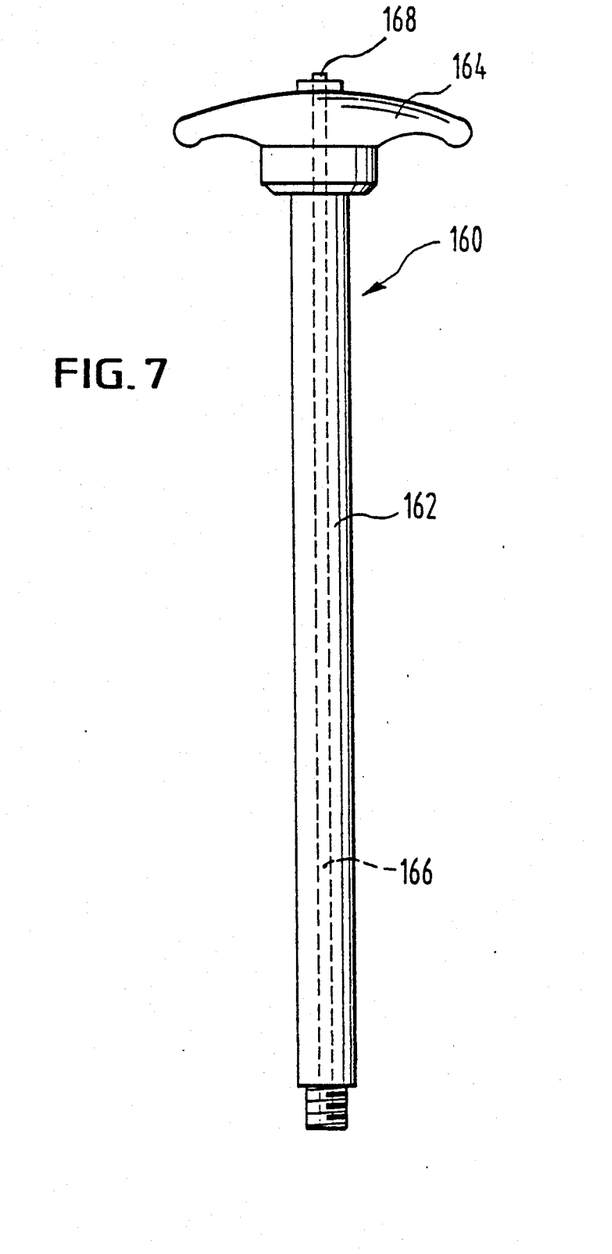
FIG. 7: a manipulation apparatus for the apparatus according to FIGS. 3 to 6, and FIG. 8: a further embodiment of the apparatus of the invention in the position as shown in FIG. 3 comprising an additional vacuum lead.

FIG. 7 illustrates a suitable manipulation apparatus 160 comprising a rod 162 and a handle 164. The manipulation apparatus has a continuous inner feed-through 166 and a vacuum connection 168 for flange-mounting a vacuum pump. The gas is removed from the mixing system by evacuating it.

Figure 8:
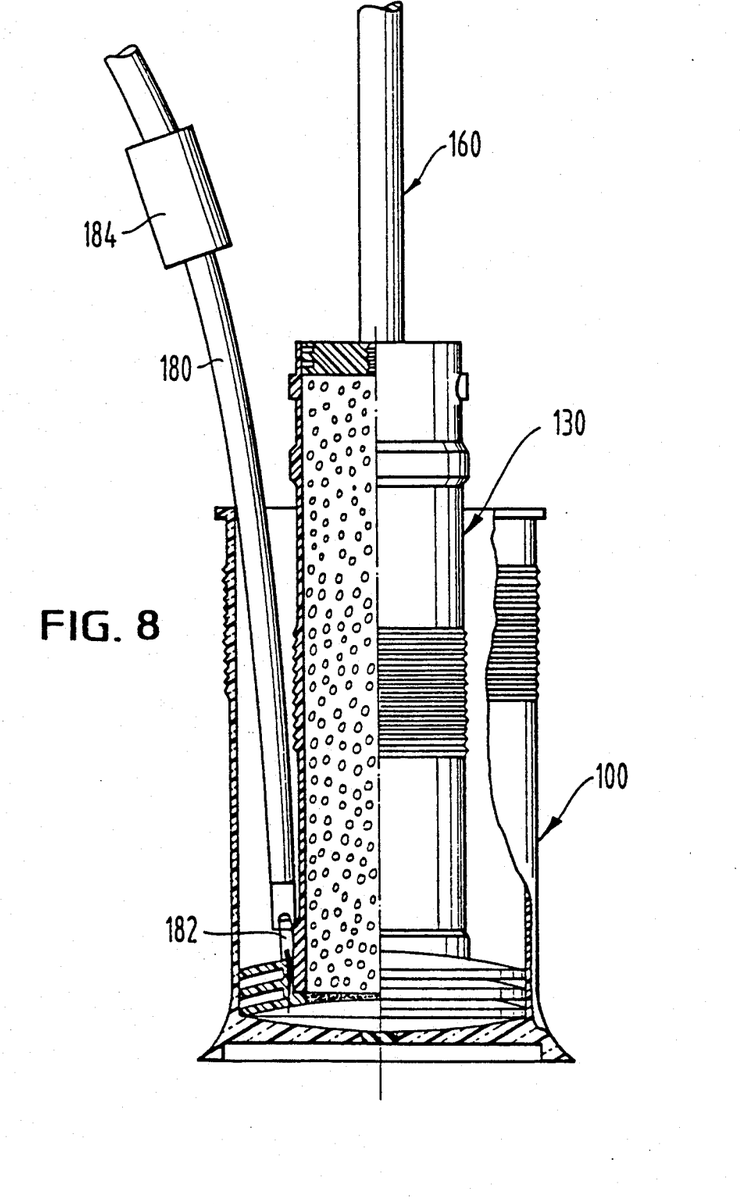

According to FIG. 8, which shows the apparatus in the same position as FIG. 3, it is also possible to provide a vacuum lead 180 connected directly to the provided valve 182 instead of the valve 146 in FIG. 3. Evacuation can be carried out via the lead 180 by inserting a charcoal filter 184. In this embodiment, the air and other gases are sucked out of the mixing bowl 100, whereas in the embodiment of FIG. 7, they are sucked straight out of the applicator 130.

The invention is not restricted to the above examples which refer to mixing bone cement and filling it into an applicator, but can be generally used to mix a compound comprising at least two components and to fill the mixed compound into a vessel. Thus the examples of the apparatus of the invention described above can be generally used to mix a compound comprising at least two components and to fill the compound into a vessel.

In the examples described above, the relative motion of the first vessel, the second vessel and, optionally, the plunger is necessary for mixing and filling in the compound; said motion is carried out by hand. It is, of course, possible to achieve the mixing and filling principle of the invention, especially in systems which have a large mixing volume, by moving the individual parts mechanically. For this, one could for instance provide two driving means, one of which is detachably engageable with the second vessel (applicator) and the other with the plunger or its manipulation apparatus. By alternately grasping and moving the second vessel or the plunger in an axial direction and at the same time letting go of the respective other, freely movable part, it is possible to induce a double relative motion of the two vessels when holding down the first vessel (mixing vessel) at the same time, said motion resulting in the compound to be mixed being moved back and forth between the two vessels and in its being thoroughly mixed. It is also possible to provide two driving means which act in opposite directions, one for the first vessel (mixing vessel) and one for the plunger or its manipulation apparatus, by means of which the first vessel and the plunger are alternately moved towards each other in an axial direction. These driving means must be detachable, too, and, furthermore, this embodiment comprises a means for detachably holding the second vessel (applicator). An apparatus of this kind also renders it possible to achieve the flow motion of the compound between the first and the second vessel through the opening of the second vessel, which motion is necessary for the process of extrusion mixing as explained above.

I claim:

1. An apparatus for mixing a compound containing at least two components, comprising:
   a first vessel closed at one end thereof;

a second vessel, the cross-section of which is smaller than that of the first vessel, the second vessel having an opening at one end thereof and being movable within the first vessel relative thereto; and a sealing means at the outer circumference of the second vessel at its open end which seals off the space between the inner circumference of the first vessel and the outer circumference of the second vessel for the compound and its components so that the components are mixed and the compound is extruded into the second vessel when the two vessels are moved relative to each other, by pushing the second vessel with its open end into the first vessel.

2. The apparatus according to claim 1, further comprising a plunger which is movable within the second vessel.

3. A process for mixing a compound containing at least two components wherein the compound is introduced into a first vessel and is then repeatedly pushed through an opening into a second vessel and back again into said first vessel by means of an opposite motion of said vessels, both vessels being made of a rigid material.

4. An apparatus for mixing bone cement and filling it into an applicator, said apparatus comprising:
an applicator;
a mixing bowl, the cross-section of which is larger than that of the applicator and in which the applicator is insertable with one of its ends and can be moved relative to the mixing bowl; and
a sealing means which can be connected to the applicator and seals off the outer surface of the applicator and the inner surface of the mixing bowl in a cement-tight manner so that the bone cement cannot flow between the outer surface of the applicator and the inner surface of the mixing bowl.

5. The apparatus according to claim 4, further comprising a lid for sealing the mixing bowl in a vacuum-tight manner, the lid having a plug for connecting a vacuum lead.

6. The apparatus according to claim 5, wherein the lid has a firm rim and an inner portion made of flexible material and comprising a feed-through for the introduction of a round rod.

7. The apparatus according to claim 4, further comprising a plunger which is movable within the applicator, in a cement-tight manner so that the bone cement cannot flow between the outer surface of the plunger and the inner surface of the applicator.

8. The apparatus according to claim 7, further comprising a manipulation means which can be connected to the plunger.

9. The apparatus according to claim 7, further comprising a membrane for sealing off the end of the applicator which is insertable into the mixing bowl.

10. The apparatus according to claim 4, wherein the mixing bowl is cylindrical and has a bottom, the interior of which is concave.

11. The apparatus according to claim 4, wherein the mixing bowl is cylindrical and has a bottom, the interior of which is rounded.

12. The apparatus according to claim 4, wherein the sealing means comprises at least one valve to let out gas.

13. The apparatus according to claim 4, wherein the sealing means comprises a cylindrical member having several flexible lamellae on its outer circumference which contact the inner circumference of the mixing bowl.

14. The apparatus according to claim 1, wherein at least the foremost lamella which faces the bottom of the mixing bowl is concave.

15. The apparatus according to claim 4, further comprising a third vessel which receives the monomer and is connectable to the mixing bowl, the monomer vessel comprising a needle and the bottom of the mixing bowl comprising a reclosable plug which can be pierced by the needle.

16. The apparatus according to claim 4, further comprising a mouthpiece which is connectable to one end of the applicator.

17. The apparatus according to claim 4, further comprising a means for evacuating the mixing bowl.

18. The apparatus according to claim 4, further comprising a means for evacuating the applicator.

19. A process for mixing bone cement consisting of liquid monomer and polymer powder and filling it into an applicator, the process comprising the steps of introducing the liquid monomer and the polymer powder into a mixing bowl, mixing said liquid monomer and said polymer powder to form a mixture and then extruding said mixture through an opening of said mixing bowl into said applicator, by means of compression applied to said mixture.

* * * * *

UNITED STATES PATENT AND TRADEMARK OFFICE
CERTIFICATE OF CORRECTION

PATENT NO. : 5,015,101

DATED : May 14, 1991

INVENTOR(S) : Klaus Draenert

It is certified that error appears in the above-identified patent and that said Letters Patent is hereby corrected as shown below:

Col. 12, line 22, delete "claim 1", insert --claim 13--.

Signed and Sealed this

Fifteenth Day of September, 1992

Attest:

DOUGLAS B. COMER

*Attesting Officer*    *Acting Commissioner of Patents and Trademarks*